(12) United States Patent
Baril et al.

(10) Patent No.: US 11,344,284 B2
(45) Date of Patent: May 31, 2022

(54) TISSUE SPECIMEN RETRIEVAL DEVICE WITH VARIABLE BAG BRIM

(71) Applicant: Covidien LP, Mansfield, MA (US)

(72) Inventors: Jacob C. Baril, Norwalk, CT (US);
Justin Thomas, New Haven, CT (US);
Saumya Banerjee, Hamden, CT (US);
Roy Pilletere, North Haven, CT (US);
Matthew Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 64 days.

(21) Appl. No.: 16/787,136

(22) Filed: Feb. 11, 2020

(65) Prior Publication Data
US 2021/0244392 A1     Aug. 12, 2021

(51) Int. Cl.
*A61B 17/00* (2006.01)

(52) U.S. Cl.
CPC .............. *A61B 17/00234* (2013.01); *A61B 2017/00287* (2013.01); *A61B 2017/00867* (2013.01); *A61B 2017/00991* (2013.01)

(58) Field of Classification Search
CPC .... A61B 17/00234; A61B 2017/00287; A61B 2017/00867; A61B 2017/00991; A61B 2017/00358; A61B 17/221; A61B 17/32056
See application file for complete search history.

(56) References Cited

U.S. PATENT DOCUMENTS

| | | | |
|---|---|---|---|
| 5,735,289 A * | 4/1998 | Pfeffer | A61B 17/00234 600/562 |
| 6,059,793 A | 5/2000 | Pagedas | |
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |
| 6,344,026 B1 | 2/2002 | Burbank et al. | |
| 6,350,266 B1 | 2/2002 | White et al. | |
| 6,350,267 B1 | 2/2002 | Stefanchik | |

(Continued)

*Primary Examiner* — Brooke Nicole Labranche
(74) *Attorney, Agent, or Firm* — Carter, Deluca & Farrell LLP

(57) ABSTRACT

A tissue specimen retrieval device includes a first shaft having a first end of a bag brim for supporting a tissue specimen bag attached thereto and a second shaft including a second end of the bag brim attached thereto. The second shaft is telescopically movable within the first shaft between a retracted position, wherein the bag brim is disposed within the first shaft, a first deployed position, wherein a portion of the second end of the bag brim deploys distally from the first shaft forming a substantially circular enclosure having a first diameter for supporting the tissue specimen bag thereon, and one or more further deployed positions wherein the portion of the second end of the bag brim deploys further distally from the first shaft increasing the diameter of the substantially circular enclosure for supporting the tissue specimen bag thereon.

20 Claims, 3 Drawing Sheets

(56) References Cited

U.S. PATENT DOCUMENTS

| | | |
|---|---|---|
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,645,283 B2 | 1/2010 | Reynolds et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinsk et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,452 B2 | 10/2016 | Menn et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,629,618 B2 | 4/2017 | Davis et al. |
| 9,642,638 B1 | 5/2017 | Carrier |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2006/0229640 A1* | 10/2006 | Whitfield ............ A61B 17/221 606/114 |
| 2011/0184431 A1* | 7/2011 | Parihar .................. A61B 17/00 606/114 |

\* cited by examiner

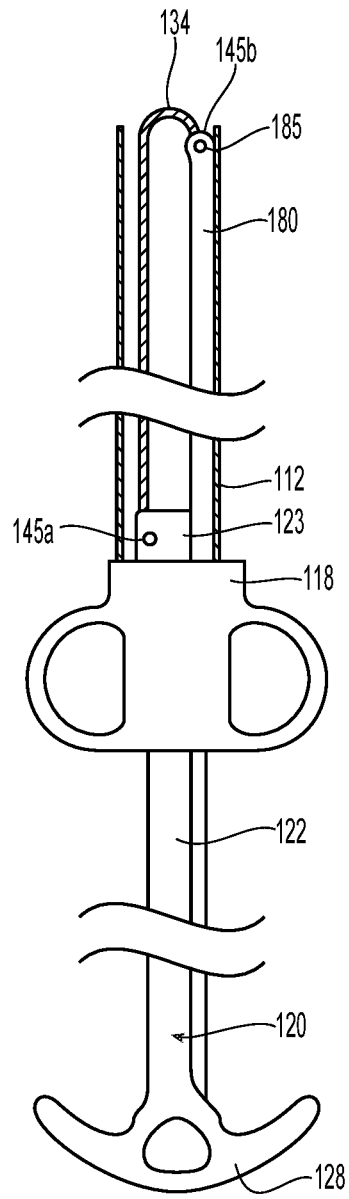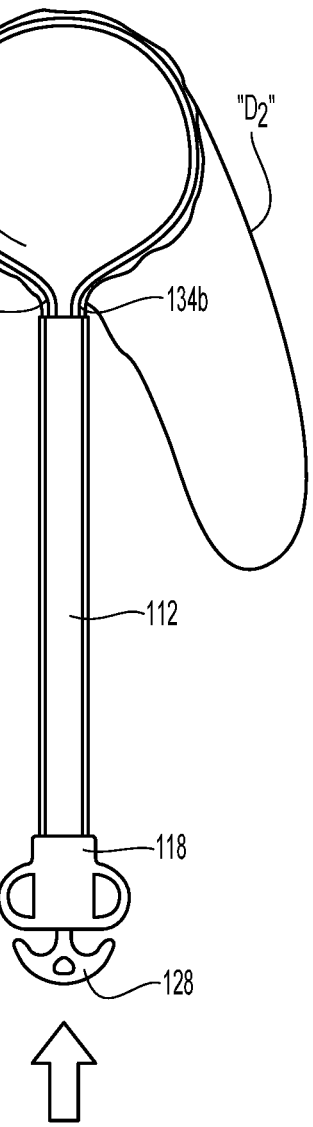
Fig. 3       Fig. 4A       Fig. 4B

TISSUE SPECIMEN RETRIEVAL DEVICE WITH VARIABLE BAG BRIM

BACKGROUND

Technical Field

The present disclosure relates to tissue specimen retrieval from an internal body cavity and, more particularly, to tissue specimen retrieval devices and methods to facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment. As a result, various specimen retrieval devices have been developed. These devices are typically made from shape memory alloys (e.g., Nitinol®) that are configured to facilitate deployment of the specimen bag and bag brim for specimen retrieval. However, these materials tend to be expensive compared to stainless steel and other materials.

Moreover, specimen retrieval devices often come from the manufacturer preloaded with a bag brim of a specific diameter which in most cases is over-sized for the tissue specimen.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

Provided in accordance with aspects of the present disclosure is a tissue specimen retrieval device, including a first shaft having a first end of a bag brim for supporting a tissue specimen bag attached thereto and a second shaft including a second end of the bag brim attached thereto. The second shaft is telescopically movable within the first shaft between a retracted position, wherein the bag brim is disposed within the first shaft, a first deployed position, wherein a portion of the second end of the bag brim deploys distally from the first shaft forming a substantially circular enclosure having a first diameter for supporting the tissue specimen bag thereon, and one or more further deployed positions wherein the portion of the second end of the bag brim deploys further distally from the first shaft increasing the diameter of the substantially circular enclosure for supporting the tissue specimen bag thereon.

In aspects according to the present disclosure, the first end of the bag brim is fixed to the first shaft about a fixed pivot. In other aspects according to the present disclosure, the second end of the bag brim is fixed to the second shaft about a dynamic pivot and movement of the second shaft relative to the first shaft moves the dynamic pivot along with the second shaft to deploy the bag brim.

In aspects according to the present disclosure, during movement of the second shaft relative to the first shaft, the first end of the bag brim is configured to rotate about the fixed pivot. In other aspects according to the present disclosure, during movement of the second shaft relative to the first shaft, the second end of the bag brim is configured to rotate about the dynamic pivot.

In aspects according to the present disclosure, the second end of the bag brim is fixed to the second shaft about a dynamic pivot and movement of the second shaft relative to the first shaft moves the dynamic pivot along with the second shaft to deploy the bag brim and wherein during movement of the second shaft relative to the first shaft, the first end of the bag brim is configured to rotate about the fixed pivot and the second end of the bag brim is configured to rotate about the dynamic pivot.

In aspects according to the present disclosure, a drive coupling is configured to operably couple the second end of the bag brim to the second shaft.

In aspects according to the present disclosure, the bag brim is made from a shape memory alloy. In other aspects according to the present disclosure, the bag brim is made from a material selected from a group consisting of polymers, plastics, composite materials, surgical stainless steel, and aluminum. In still other aspects according to the present disclosure, the shape memory alloy, polymer, plastic, composite material, stainless steel or aluminum is biased or pre-formed in a substantially circular shape.

In aspects according to the present disclosure, the diameter of the bag brim in the first deployed position is about two inches. In other aspects according to the present disclosure, when the second shaft is fully approximated relative to the first shaft the bag brim and tissue specimen bag are fully deployed. In yet other aspects according to the present disclosure, when the bag brim and tissue specimen bag are fully deployed the diameter of the bag brim is about six inches. In still other aspects according to the present disclosure, the diameter of the bag brim varies in the range of about two inches to about six inches when transitioning from the first deployed position to the fully deployed position.

Provided in accordance with aspects of the present disclosure is a tissue specimen retrieval device, including a first shaft having a first end of a bag brim for supporting a tissue specimen bag attached thereto and a second shaft including a second end of the bag brim attached thereto. The second shaft is telescopically movable within the first shaft between a retracted position, wherein the bag brim is disposed within the first shaft, a first deployed position, wherein a portion of the second end of the bag brim deploys distally from the first shaft forming a substantially circular enclosure having a first diameter for supporting the tissue specimen bag thereon, and a series of subsequent, incrementally deployed positions wherein further distal movement of the second shaft relative to the first shaft deploys the second end of the bag brim further distally from the first shaft varying the diameter of the substantially circular enclosure.

In aspects according to the present disclosure, the first end of the bag brim is fixed to the first shaft about a fixed pivot. In other aspects according to the present disclosure, the second end of the bag brim is fixed to the second shaft about a dynamic pivot and movement of the second shaft relative to the first shaft moves the dynamic pivot along with the second shaft to deploy the bag brim.

In aspects according to the present disclosure, a drive coupling is configured to operably couple the second end of the bag brim to the second shaft. In other aspects according to the present disclosure, the bag brim is made from a shape memory alloy. In yet other aspects according to the present disclosure, the diameter of the bag brim varies in the range of about two inches to about six inches when transitioning from the first deployed position to the fully deployed position.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

FIG. 3 is a top, internal view of the tissue specimen retrieval device of FIG. 1 showing a fixed pivot at a distal end thereof and a dynamic pivot at a proximal end thereof;

FIG. 4A is a top view of the tissue specimen retrieval device of FIG. 1 in a partially deployed position resulting in the bag brim with a first diameter; and FIG. 4B is a top view of the tissue specimen retrieval device of FIG. 1 in a fully deployed position resulting in the bag brim with a second, larger diameter.

DETAILED DESCRIPTION

Figure 1:
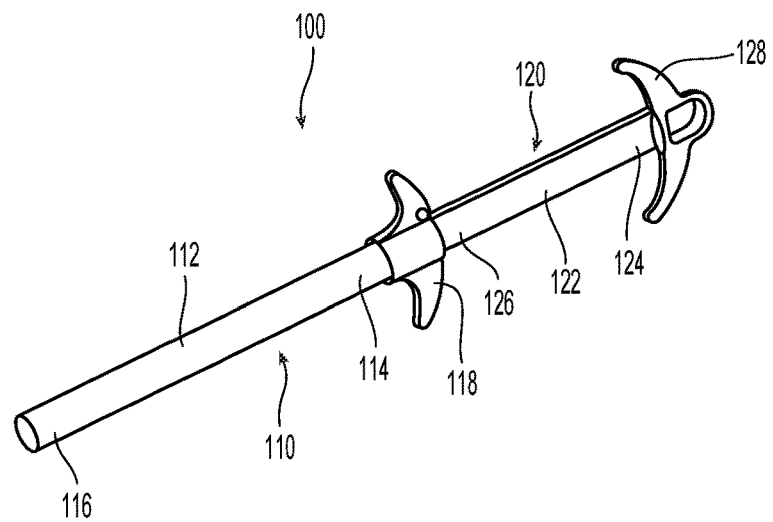
FIG. 1 is a perspective view of a tissue specimen retrieval device provided in accordance with aspects of the present disclosure, disposed in a retracted position.

Turning to FIGS. 1-3, a tissue specimen retrieval device provided in accordance with the present disclosure is shown generally identified by reference numeral 100. Tissue specimen retrieval device 100 includes a first body 110, a second body 120, and an end effector assembly 130 including a bag brim 140 and a specimen bag 160. First body 110 includes a first shaft 112 defining a proximal end portion 114 and a distal end portion 116. First body 110 further includes a first handle 118 disposed at proximal end portion 114 of first shaft 112. First handle 118 may be engaged with proximal end portion 114 of first shaft 112, monolithically formed with proximal end portion 114 of first shaft 112, or otherwise secured thereto in any suitable manner that enables a user to grasp and manipulate first handle 118 to thereby control manipulation of first shaft 112.

Second body 120 includes a second shaft 122 defining a proximal end portion 124 and a distal end portion 126. Second shaft 122 supports end effector assembly 130 at distal end portion 126 of second shaft 122 and is telescopically slidably within and relative to first shaft 112 between a retracted position of tissue specimen retrieval device 100 (FIG. 1), wherein end effector assembly 130 is disposed within first shaft 112, and a deployed position of tissue specimen retrieval device 100 (FIG. 2A), wherein end effector assembly 130 extends distally from first shaft 112 to deploy the bag brim 140 and specimen bag 160. Second body 120 further includes a second handle 128 disposed at proximal end portion 124 of second shaft 122. Second handle 128 may be engaged with proximal end portion 124 of second shaft 122, monolithically formed with proximal end portion 124 of second shaft 122, or otherwise secured thereto in any suitable manner that enables a user to grasp and manipulate second handle 128 to thereby control manipulation of second shaft 122. Second handle 128, more specifically, is movable relative to first handle 118 from a spaced-apart position (FIG. 1) to an approximated position (FIG. 2A) to move tissue specimen retrieval device 100 from the retracted position (FIG. 1), wherein end effector assembly 130 is disposed within first shaft 112, to the deployed position (FIG. 2A), wherein end effector assembly 130 extends distally from first shaft 112.

Figure 2A:
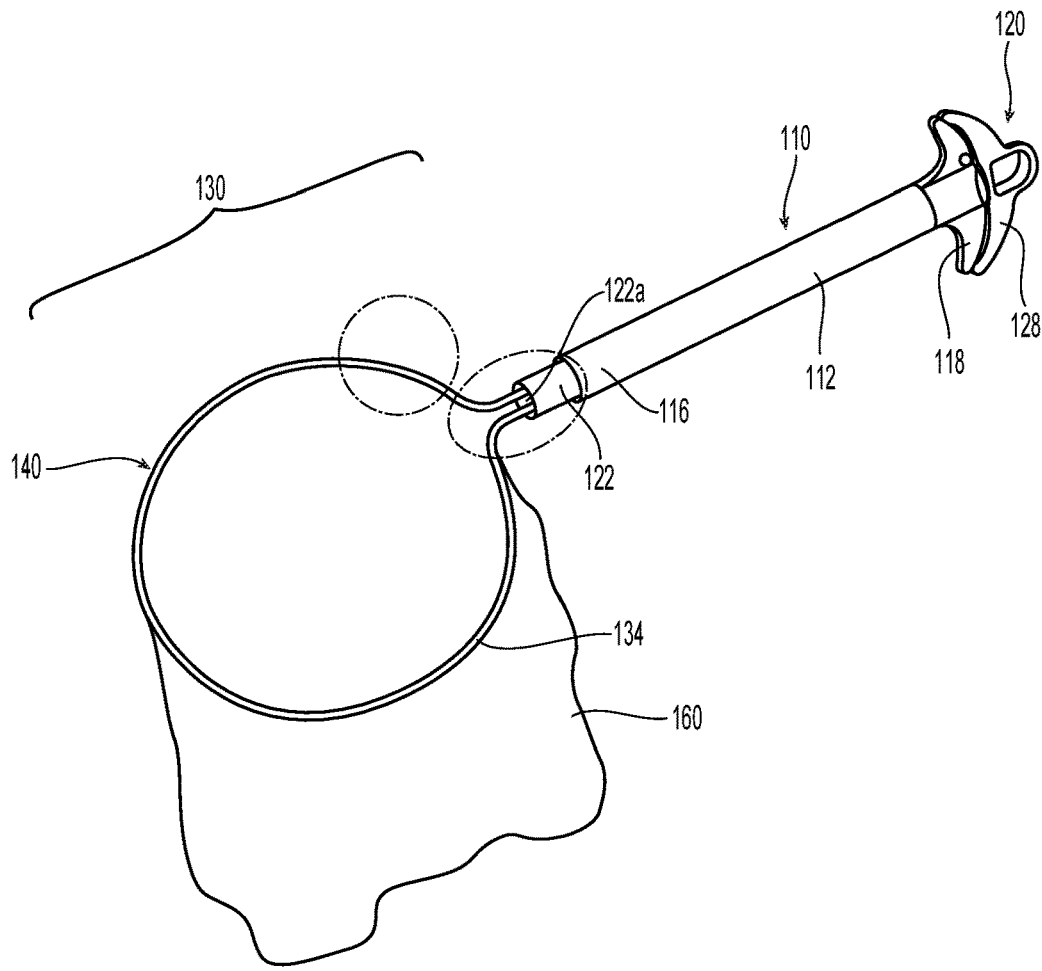
FIG. 2A is a perspective view of the tissue specimen retrieval device of FIG. 1, disposed in a deployed position showing a bag brim supporting a specimen bag.
Figure 2B:
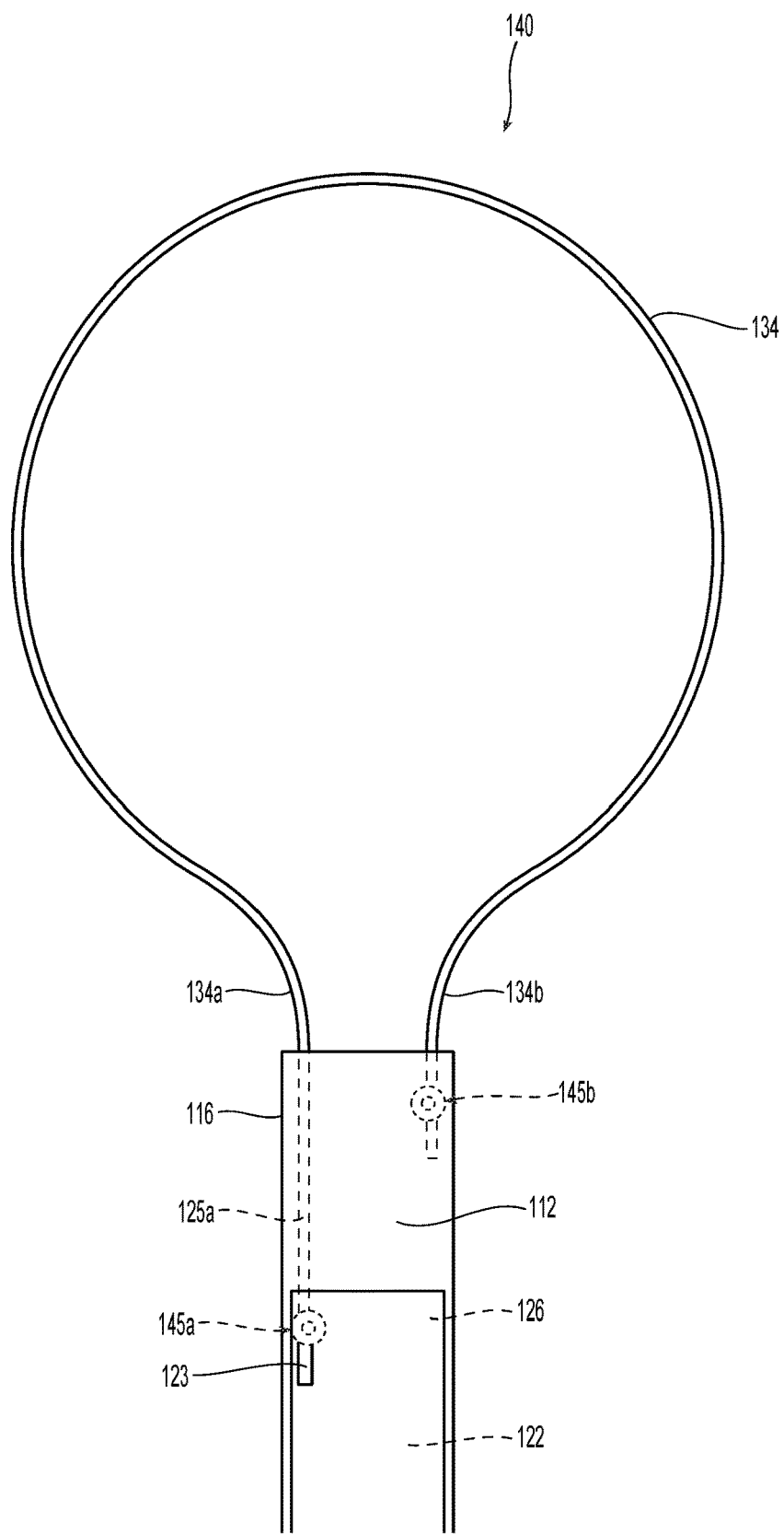
FIG. 2B is a top view of the bag brim of FIG. 2A showing a reinforced spring assembly.

Referring to FIGS. 2A-2B, end effector assembly 130, as noted above, is supported at distal end portion 126 of second shaft 122. End effector assembly 130, more specifically, includes bag brim 140 extending distally from distal end portion 126 of second shaft 122 and a specimen bag 160 supported on the bag brim 140. Bag brim 140 includes a substantially circular arm 134 that extends from a distal face 122a of shaft 122. Bag brim 140 is typically made from a shape memory alloy (e.g., Nitinol®) that is configured to facilitate deployment of the bag brim 140 for specimen retrieval. Other types of materials may be cheaper to utilize for the bag brim 140, e.g., polymers, plastics, composite materials, surgical stainless steel, aluminum, etc., but may need to be reinforced with a spring assembly (not shown) to insure reliable deployment. Moreover, the bag brim 140 may be designed to be substantially flat (e.g., thin, band-like material) to provide strength for supporting the specimen bag 160 while still being flexible to facilitate expansion and retraction thereof.

For example and as best shown in FIGS. 2A-2B, bag brim 140 is made from high yield stainless steel that may be heat treated after initial shaping. More specifically, arm 134 includes free ends 134a and 134b that operably engage respective distal ends 116, 126 of shafts 112, 122 to form a band-like support for supporting the specimen bag 160.

For certain types of surgery, e.g., OBGYN procedures, tissue specimens can range from 300 grams to 1500 grams requiring differently-sized openings in the bag 160. Typically a "one size fits all" approach may unduly limit a surgeon visibility, may be cumbersome and may unnecessarily reduce valuable operating space. As such and with continued reference to FIGS. 2A-2B, free ends 134a, 134b are configured to cooperate with a corresponding series of pivots to deploy the bag brim 140 in a variably-sized manner. More specifically, end 134a is configured to operably couple to a dynamic pivot 145a which, in turn, connects to a drive coupling 123 disposed at the distal end 126 of the second shaft 122. End 134b is configured to operably couple to a fixed pivot 145b that is anchored to shaft 112 proximate the distal end 116 thereof.

Actuation of handle 128 towards handle 118 translates shaft 122 distally within shaft 112 and causes drive coupling 123 to push end 134a distally to expose arm 134 of bag brim 140 from end 116 of shaft 112. End 134b is fixed to distal end 116 but remains rotatable about pivot 145b during deployment of arm 134. Rotation of end 134b facilitates deployment of arm 134 as the drive coupling 123 is pushed distally to expose of arm 134. End 134a may also be configured to rotate about pivot 145a during deployment of arm 134. Allowing both ends 134a, 134b to freely rotate about respective pivots 145a, 145b as needed may facilitate deployment.

Turning now to FIGS. 4A and 4B, variable deployment of the bag brim 140 is shown and described. When a user initially approximates handle 128 towards handle 118, drive coupling 123 forces dynamic pivot 145a and end 134a of arm 134 distally while end 134b remains fixed thereby exposing the bag 160 and a portion of arm 134 having a first diameter (FIG. 4A). Continued movement of handle 128 towards handle 118 exposes incrementally more of arm 134 from distal end 116 thus increasing the size of the diameter of arm 134 enabling larger tissue specimens to be captured within bag 160 (FIG. 4B). As such, the surgeon can easily regulate the size of the opening of the bag 160 depending upon any particular purpose or to achieve any particular result. Bag brims 140 with openings having diameters that vary in the range of about two inches (2") to about six inches (6") are contemplated. Other larger or smaller openings may be suitable for a particular purpose.

As mentioned above, the bag brim 140 may be made from a shape memory alloy, e.g., Nitinol®, that may be biased in a substantially circular shape. As such, by exposing more of the end 134a of arm 134 from the distal end 116, the substantially circular shape of the bag brim 140 is maintained while the overall diameter expands.

Once a tissue specimen is captured within the bag 160, handle 128 may be retracted or pulled proximally relative to handle 118 to pull end 134a back within shaft 112 and reduce the diameter of the bag brim 140. Bag brim 140 may include features that close off the opening of the bag brim 140 when fully retracted. Other features may be included that sever the bag brim 140 from the bag 160 when fully retracted.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
a first shaft including a first end of a bag brim for supporting a tissue specimen bag attached thereto;
a second shaft defining a lumen, the second shaft including a second end of the bag brim attached to the second shaft within the lumen of the second shaft, the second shaft telescopically movable within the first shaft between a retracted position, wherein the bag brim is disposed within the first shaft, a first deployed position, wherein at least a portion of the second end of the bag brim deploys distally from the first shaft forming a substantially circular enclosure having a first diameter for supporting the tissue specimen bag thereon, and at least one further deployed position wherein the at least a portion of the second end of the bag brim deploys further distally from the first shaft increasing the diameter of the substantially circular enclosure for supporting the tissue specimen bag thereon, wherein the first end of the bag brim is fixed to the first shaft about a fixed pivot.

2. The tissue specimen retrieval device according to claim 1 wherein the second end of the bag brim is fixed to the second shaft about a dynamic pivot and movement of the second shaft relative to the first shaft moves the dynamic pivot along with the second shaft to deploy the bag brim.

3. The tissue specimen retrieval device according to claim 2 wherein during movement of the second shaft relative to the first shaft, the second end of the bag brim is configured to rotate about the dynamic pivot.

4. The tissue specimen retrieval device according to claim 1 wherein during movement of the second shaft relative to the first shaft, the first end of the bag brim is configured to rotate about the fixed pivot.

5. The tissue specimen retrieval device according to claim 1 wherein the second end of the bag brim is fixed to the second shaft about a dynamic pivot and movement of the second shaft relative to the first shaft moves the dynamic pivot along with the second shaft to deploy the bag brim and wherein during movement of the second shaft relative to the first shaft, the first end of the bag brim is configured to rotate about the fixed pivot and the second end of the bag brim is configured to rotate about the dynamic pivot.

6. The tissue specimen retrieval device according to claim 1 further comprising a drive coupling configured to operably couple the second end of the bag brim to the second shaft.

7. The tissue specimen retrieval device according to claim 1 wherein the bag brim is made from a shape memory alloy.

8. The tissue specimen retrieval device according to claim 7 wherein the shape memory alloy is biased in a substantially circular shape.

9. The tissue specimen retrieval device according to claim 1 wherein the bag brim is made from a material selected from a group consisting of polymers, plastics, composite materials, surgical stainless steel, and aluminum.

10. The tissue specimen retrieval device according to claim 1 wherein the diameter of the bag brim in the first deployed position is about two inches.

11. The tissue specimen retrieval device according to claim 1 wherein when the second shaft is fully approximated relative to the first shaft the bag brim and tissue specimen bag are in a fully deployed position.

12. The tissue specimen retrieval device according to claim 11 wherein when the bag brim and tissue specimen bag are fully deployed the diameter of the bag brim is about six inches.

13. The tissue specimen retrieval device according to claim 11 wherein the diameter of the bag brim varies in the range of about two inches to about six inches when transitioning from the first deployed position to the fully deployed position.

14. A tissue specimen retrieval device, comprising:
a first shaft including a first end of a bag brim for supporting a tissue specimen bag attached thereto;
a second shaft defining a lumen, the second shaft including a second end of the bag brim attached to the second shaft within the lumen of the second shaft, the second shaft telescopically movable within the first shaft between a retracted position, wherein the bag brim is disposed within the first shaft, a first deployed position, wherein at least a portion of the second end of the bag brim deploys distally from the first shaft forming a substantially circular enclosure having a first diameter for supporting the tissue specimen bag thereon, and a series of subsequent, incrementally deployed positions wherein further distal movement of the second shaft relative to the first shaft deploys the second end of the bag brim further distally from the first shaft varying the diameter of the substantially circular enclosure, wherein the first end of the bag brim is fixed to the first shaft about a fixed pivot.

15. The tissue specimen retrieval device according to claim 14 wherein the second end of the bag brim is fixed to the second shaft about a dynamic pivot and movement of the second shaft relative to the first shaft moves the dynamic pivot along with the second shaft to deploy the bag brim.

16. The tissue specimen retrieval device according to claim 14 further comprising a drive coupling configured to operably couple the second end of the bag brim to the second shaft.

17. The tissue specimen retrieval device according to claim 14 wherein the bag brim is made from a shape memory alloy.

18. The tissue specimen retrieval device according to claim 14 wherein the diameter of the bag brim varies in the range of about two inches to about six inches when transitioning from the first deployed position to a fully deployed position of the incrementally deployed positions.

19. A tissue specimen retrieval device, comprising:
a first shaft including a first end of a bag brim for supporting a tissue specimen bag attached thereto; and
a second shaft defining a lumen, the second shaft including a second end of the bag brim attached to the second shaft within the lumen of the second shaft, the second shaft telescopically movable within the first shaft between a retracted position, wherein the bag brim is disposed within the first shaft, a first deployed position, wherein at least a portion of the second end of the bag brim deploys distally from the first shaft forming a substantially circular enclosure having a first diameter for supporting the tissue specimen bag thereon, and at least one further deployed position wherein the at least a portion of the second end of the bag brim deploys further distally from the first shaft increasing the diameter of the substantially circular enclosure for supporting the tissue specimen bag thereon, wherein the second end of the bag brim is fixed to the second shaft about a dynamic pivot and movement of the second shaft relative to the first shaft moves the dynamic pivot along with the second shaft to deploy the bag brim.

20. The tissue specimen retrieval device according to claim 19 wherein during movement of the second shaft relative to the first shaft, the second end of the bag brim is configured to rotate about the dynamic pivot.

* * * * *